US007125702B2

(12) United States Patent
Gowda et al.

(10) Patent No.: US 7,125,702 B2
(45) Date of Patent: Oct. 24, 2006

(54) PROCESS FOR THE PREPARATION OF ANGIOTENSIS CONVERTING ENZYME (ACE) INHIBITORS AND ITS USE

(75) Inventors: Lalitha Ramakrishna Gowda, Karnataka (IN); Appu Rao Gopal Rao Appu Rao, Karnataka (IN); Vishweshwariah Prakash, Karnataka (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 11/287,740

(22) Filed: Nov. 28, 2005

(65) Prior Publication Data

US 2006/0073543 A1    Apr. 6, 2006

Related U.S. Application Data

(63) Continuation of application No. 10/397,813, filed on Mar. 25, 2003, now abandoned.

(51) Int. Cl.
  *C12N 9/50*   (2006.01)
  *C12N 9/76*   (2006.01)
  *A61K 38/48*  (2006.01)
  *A61K 38/02*  (2006.01)

(52) U.S. Cl. .................. 435/212; 435/213; 424/94.64; 530/316; 930/40

(58) Field of Classification Search ................ 435/212, 435/213; 424/94.64; 530/316; 930/40
See application file for complete search history.

(56) References Cited

FOREIGN PATENT DOCUMENTS

| JP | 04-275298 | 9/1992 |
|----|-----------|--------|
| JP | 08-225593 | 9/1996 |

OTHER PUBLICATIONS

Wu et al., "Hypotensive and physiologic effect of angiotensin converting enzyme inhibitory peptides derived from soy protein on spontaneously hypertensive rats," J Agric Food Chem 49:501-506, 2001.
Soybean proteins, http://class.fst.ohio-state.edu/ FST822/lectures/Soy.htm, downloaded from the Internet on Nov. 10, 2004.
Abstract from Wageningen University dissertation No. 3084, Formation, structure and rheological properties of soy protein gels, Nov. 20, 2001, downloaded from the Internet on Nov. 10, 2004.

*Primary Examiner*—Robert A. Wax
*Assistant Examiner*—Rosanne Kosson
(74) *Attorney, Agent, or Firm*—Drinker Biddle & Reath LLP

(57) ABSTRACT

The invention is a process for the preparation of angiotensin converting enzyme (ACE) inhibitors and the use thereof.

7 Claims, 2 Drawing Sheets

PROCESS FOR THE PREPARATION OF ANGIOTENSIS CONVERTING ENZYME (ACE) INHIBITORS AND ITS USE

This is a continuation of co-pending application Ser. No. 10/397,813, filed Mar. 25, 2003 now abandoned, the entire disclosure of which is incorporated herein by reference.

FIELD OF THE INVENTION

The present invention relates to a process for the preparation of an enzymatic hydrolysate of a selected soybean storage protein fraction, glycinin that evidences potent Angiotensin Converting Enzyme (ACE) inhibitory activity. The present invention also relates to a use of polypeptides of glycinin as ACE inhibitors.

BACKGROUND ART

In recent years, peptides from partial enzymatic hydrolysates of food proteins produced in vivo or in vitro have received greater attention from food scientists than ever before. Many biological peptides with health benefits such as opioid activity, antihypertensive activity, antibacterial activity, mineral-binding activity, anti-thrombotic activity, anti-gastric activity, enhancement of intestinal activity, etc have been identified from food protein hydrolysates. These peptides are hidden in a latent state within the sequence of the parent protein and may be released by proteolytic processes during in vivo/in vitro digestion or during food processing. Biologically active peptides derived from daily food proteins would be useful in the development of novel functional food additives and for therapeutic uses.

Hypertension is one of the major independent risk factors for arteriosclerosis, stroke, myocardial infarction and end-stage renal disease. Angiotensin 1-converting enzyme (EC 3.4.15.1, referred to herein as 'ACE'), which is a dipeptidyl-carboxypeptidase, plays an important physiological role in regulating blood pressure. ACE raises blood pressure by converting an active form of the decapeptide, angiotensin I, to a potent vasoconstrictor octapeptide angiotensin II, the most potent naturally occurring pressor substance known. ACE also degrades vasodilative bradykinin, which has a depressor action. This enzyme also plays a physiological role in the regulation of local levels of other endogenous peptides. For these reasons, specific inhibitors of ACE are useful for regulating blood pressure in the human body. Because ACE activity is closely associated with the development of hypertension and arteriosclerosis, in vitro inhibition of ACE has been used for screening therapeutic agents. Therapeutic vasodepressors such as Captopril and D-2 methyl-3-mercaptopropanoyl-L-proline have been synthesized as ACE inhibitors. Synthetic ACE inhibitors are very potent and have adverse effects that are generally not considered safe.

Interest has recently been focused on the isolation and identification of purified ACE inhibitory peptides from various food sources or food protein hydrolysates after enzymatic digestion. An ACE inhibitor derived from food protein was first reported by Oshima et al., 1979 (Oshima, G., Shimabukuro, H and Nagasawa, K. (1979) "Peptide inhibitors of Angiotensin converting enzyme digests of gelatin by bacterial collagenase". Biochim. Biophys. Acta, 556, 128). Since then protein digests containing ACE inhibitors have been produced from a variety of edible sources including milk, eggs, chicken, pork beef, fish, and soybean, maize and micro algae (Ariyoshi, Y., (1993), "Angiotensin converting enzyme inhibitors derived from food proteins" Trends Food Sci. Technol., 4, 139–144). Peptides derived from casein and soybean protein have been developed based on the expectation of low toxicity and high safety. Peptides exhibiting ACE-inhibiting activities have been separated from enzymatic hydrolysates of casein (Japanese Laid-Open Patent publication Nos 62-270533, 64-5497, 64-83096) and soybean protein (Japanese Laid-Open Patent publication No. 3-1671981.

Soybean is a source of high quality proteins all over the world. Defatted soy meal contains nearly 50–55% protein. The major proteins of soybeans are the storage globulin classified as 2S, 7S, 11S and 15S protein based on sedimentation coefficients. The 11S fraction also known as glycinin constitutes 25–35% of the total proteins (Liu 1997, In: Soybeans: Chemistry, Technology and Utilization, pp 25–113, Chapman & Hall, New York).

Reference may be made, to the published paper of Potter, 1995 'Overview of proposed mechanisms for the hypocholesterolomic effect of soy' wherein soybean protein has been shown to have beneficial effects on preventing hyperlipidemic or hypercholesterolemic lesions, which cause arteriosclerosis and hypertension. Glycinin, which forms 25–35% of the total soy protein, is used in this invention to provide antihypertensive peptides.

Reference is made to the published paper of Yu, et al, 1996 "Effect of soybean hydrolysate on hypertension in spontaneously hypertensive rats" (J. Korean Soc. Food. Sci. Nutr. 25, 1031–1036) wherein they have demonstrated that a soybean hydrolysate exerted an inhibitory activity of ACE in vascular tissue in vivo and lowered systolic blood pressure in spontaneously hypertensive rats. The present invention uses an isolated protein fraction, glycinin, of soy protein and not total soy protein.

Reference may be made to the published paper of Shin et al, 1995 'Fractionation of angiotensin converting enzyme inhibitory peptide from soybean paste' (Korean J. Food Sci. Technol. 27, 230–234) wherein it is demonstrated that a fraction of fermented soybean paste contains ACE inhibitory components and the fraction F53 exerts a strong inhibitory activity in vitro. The present invention utilizes a purified glycinin fraction of soy protein isolate.

Reference may also be made to Shin et al, 2001, in the published paper "His-His-Leu, an angiotensin I converting enzyme inhibitory peptide derived from Korean soybean paste, exerts antihypertensive activity in vivo" (J. Agric. Food Chem., 49, 3004–3009) wherein the authors report they have isolated and identified the ACE inhibitory peptide of the F53 fraction and have confirmed the ACE inhibitory activity and blood pressure lowering activity of the purified peptide in vivo. They also show that the synthetic peptide His-His-Leu resulted in a significant pressure decrease in the aorta and triple injections of the peptide decreased the systolic blood pressure by 61 mm Hg. Reference is be made to Shin et al., U.S. Pat. No. 6,232,438, wherein a process is described for preparing a highly safe and active inhibitor having the formula His-His-Leu or His-Leu-Leu and physiologically acceptable salts thereof. The present invention however uses isolated glycinin and not soybean paste.

Reference may be made to Mimura et al, 1993, U.S. Pat. No. 5,243,027 wherein the ACE inhibitory peptides are produced by an acid hydrolysis of cell free extracts of a bacteria. The present invention uses enzymes to produce the hydrolysate and the source is a plant protein.

Reference may be made to the published papers of Maruyama and Suzuki, 1982 and Maruyama et al., 1985 (Maruyama, S and Suzuki, H, "A peptide inhibitor of angiotensin-I converting enzyme in the tryptic hydrolysate of casein." Agric. Biol. Chem, 46, 1393, (Maruyama, S., Nakagomi, K., Tomizuka, N. and Suzuki, H. "Angiotensin-I converting enzyme inhibitor derived from an enzymatic hydrolysate of Casein. II Isolation and bradykinin potentiating activity on the uterus and ileum of rats" (Agric. Biol. Chem., 49, 1405) wherein they have demonstrated that a penta-peptide and hepta-peptide purified from a tryptic hydrolysate of casein inhibited ACE.

Wu and Ding, 2001 in their published paper 'Hypotensive and physiological effect of angiotensin converting inhibitory peptides derived from soy protein on spontaneously hypertensive rats' (J. Agric. Food Chem., 49, 501–505) have demonstrated in vivo hypotensive activity of soy-protein derived ACE inhibitory peptide powder at a dosage of 100 mg/kg of body weight/day/for 4-week feed in spontaneously hypertensive rats. Reference may also be made to the published paper of Wu and Ding, 2002 'Characterization of inhibition and stability of soy-protein-derived angiotensin I-converting enzyme inhibitory peptides' (Food Research International, 35, 367–375) that a soy protein alkaline hydrolysate after ultra-filtration had a $IC_{50}$ value of 0.065 mg of protein/mL. Two of the most potent peptides were Ap-Leu-Pro and Asp-Gly with $IC_{50}$ values of 4.8 and 12.3 μM respectively. The present invention however uses glycinin, a fraction of total soy protein and uses various proteases other than Alcalase.

Miyoshi et al, 1991 in their published paper 'Structures and activity on angiotensin-converting enzyme inhibitors in an α-zein hydrolysate' (Agric. Biol. Chem., 55, 1313–1318, Agric. Biol. Chem., 55, 1221, Agric. Biol. Chem., 55, 1407) isolated peptides from a thermolysin hydrolysate of α-zein, the major component of maize endospem protein and showed they inhibit ACE. The tripeptides Leu-Arg-Pro, Leu-Ser-Pro, Leu-Asn-Pro had $IC_{50}$ values of 0.27, 1.7, 1.9 μM respectively. The hypotensive activity of the synthetic peptide Leu-Arg-Pro on spontaneously hypertensive rats indicated that the blood pressure was decreased by 15 mm Hg after a 30 mg/kg intravenous injection. The present invention uses glycinin, the storage protein of soyabean.

Reference may be made to yet another published paper by Sato et al., 2002 (J. Agric. Food Chem., 50, 6245–6252) wherein the isolation and identification of ACE inhibitory peptides from the Protease S 'Amano' digest of the brown seaweed, Wakame (*Undaria pinnatifida*) and investigation on the resistance of these peptides to gastrointestinal proteases in vitro is reported. The blood pressure of spontaneously hypertensive rats decreased after a single oral dose of 1 mg/kg of body weight. The present investigation uses proteases other than Protease S'Amano' to produce the hydrolysate. Furthermore the ACE inhibitory peptides are obtained from glycinin the major storage protein of soybean.

Reference may also be made to the paper published by Hsu et al., 2002 (J. Agric. Food Chem., 50, 6109–6113) wherein they report the peptic hydrolysates of dioscorin, the storage protein of the tuber yam (*Dioscorea alata* cv Tainong) exhibited ACE inhibition. The storage protein used in the present invention is from legumes and the enzymes used to prepare the hydrolysate are other than pepsin.

Further more several patents (U.S. Pat. Nos. 5,510,331, 5,106,834, 4,914,129, 4,889,869, 4,798,821, 4,758,584, 4,703,043, 4,385,050, 4,191,753, 4,013,791) describe the preparation of synthetic peptides and peptide analogs as ACE inhibitors. The present invention describes the process for an enzymatic hydrolysate of a plant protein as an ACE inhibitor.

Furthermore numerous patents on ACE peptides ranging from tri- to nonapeptides have been published: U.S. Pat. Nos. 5,449,661, 5,071,955, 4,692,459, 4,585,758, 4,512, 979, 4,191,753, EP 174162; Japanese laid-Open Patent Publication Nos 5-2994844, 5-262790, 4-247100. However none relate to the use of glycinin as the source of antihypertensive peptides.

Enzymatic hydrolysis seems to be the most appropriate method for preparation of tailor made ACE inhibitory peptides, not only because of their large-scale commercial availability but also because of the high quality of such products. Such hydrolysates are complex mixtures of peptide species containing one or more active constituents in low concentration. Although most peptides that exhibit ACE inhibitory activity are those that are isolated and characterized, it is the extensive and expensive protocols that are limiting factors. However from the point of view of commercialization it will be the mixture of peptides, not a single purified peptide, which would be applied as a health-enhancing ingredient for use in 'physiologically functional foods'.

OBJECTS OF THE INVENTION

The main object of the present invention is to provide a process for the preparation of an enzymatic hydrolysate of a selected soybean storage protein fraction that evidences potent ACE inhibitory activity.

Another object of the present invention is to use a protein fraction, glycinin, whose amino acid sequence is known.

Yet another object of the present invention is to use different proteases to prepare the hydrolysate.

Still another object of the present invention is to use a plant protease with specificity of cleaving C-terminal to proline.

Yet another object of the present invention is to purify the ACE inhibitory peptides by reverse phase HPLC.

Another object of the present invention is to provide a use of glycinin polypeptides as ACE inhibitors.

SUMMARY OF THE INVENTION

The present invention provides a process for the preparation of an enzymatic hydrolysate of a selected soybean storage protein fraction that evidences potent Angiotensin Converting Enzyme (ACE) inhibitory activity. The present invention also provides a use of polypeptides of glycinin as ACE inhibitors.

DETAILED DESCRIPTION OF THE INVENTION

Accordingly, the present invention provides a process for the preparation of Angiotensin Converting Enzyme (ACE) inhibitory peptides from glycinin of defatted soy flour, said process comprising the steps of:

1. isolating glycinin from defatted soy flour;
2. dispersing 10–25% solution glycinin in a buffer;
3. hydrolyzing the mixture with proteolytic enzyme (2–4% w/v);
4. incubating the mixture at 37–50° C. for a period of 16–18 hours;
5. arresting the reaction by adding trichloroacetic acid (TCA-100%);
6. centrifuging the mixture at 15–20,000 rpm for 30–40 minutes, at a temperature of about 4–8° C.; and
7. obtaining a mixture of protein hydrolysates containing polypeptides;
8. separating and purifying the active peptide fractions designated as 2, 3 & 4 having ACE inhibitory activity.

In an embodiment of the present invention, glycinin is isolated protein fraction from defatted soy flour.

In another embodiment of the present invention, the buffer of step (a) is selected from Tris-HCl and sodium phosphate.

In still another embodiment of the present invention, in step (a) the pH is maintained in the range of 6.2–8.2 and a molarity of 0.05–0.1M.

In yet another embodiment of the present invention, different proteases are used to prepare the hydrolysate.

In still another embodiment of the present invention, a plant protease with specificity of cleaving C-terminal to proline is used.

In yet another embodiment of the present invention, the proteolytic enzymes are fungal proteases selected form *Aspergillus niger*, bovine trypsin, bovine chymotrypsin or plant protease or a protease from ginger (*Zingiber officinale*) or a combination of the above.

In a further embodiment of the present invention, the step (h) is performed by RP-HPLC on an octadecyl column using a linear gradient of 0.1% TFA and 70% acetonitrile.

The present invention also provides a use of the polypeptide fractions having Angiotensin Converting Enzyme (ACE) inhibitory properties.

In an embodiment of the present invention, the ACE inhibitory activity of the fractions 2, 3 & 4 is 66, 81 and 75% respectively.

In another embodiment of the present invention, the $IC_{50}$ value of in vitro ACE inhibition is in the range of 5–39 μg $N_2$ equivalence. In an embodiment of the present invention, the supernatant may be the hydrolysate containing the ACE inhibitory activity.

Isolation of Glycinin for Soy Flour

An aqueous slurry of 10–15% defatted soya flour (w/v) is prepared containing α-mercaptoethanol (0.1% v/v). The slurry is extracted by stirring for 4–6 hours at an ambient temperature. The slurry is centrifuged at 6000–8000 rpm for 30–45 minutes at an ambient temperature. Glycinin is precipitated from the supernatant by adding solid $MgCl_2$ to a final concentration of 5 mM. The precipitated glycinin is collected by centrifugation and freeze-dried.

Figure 1A:
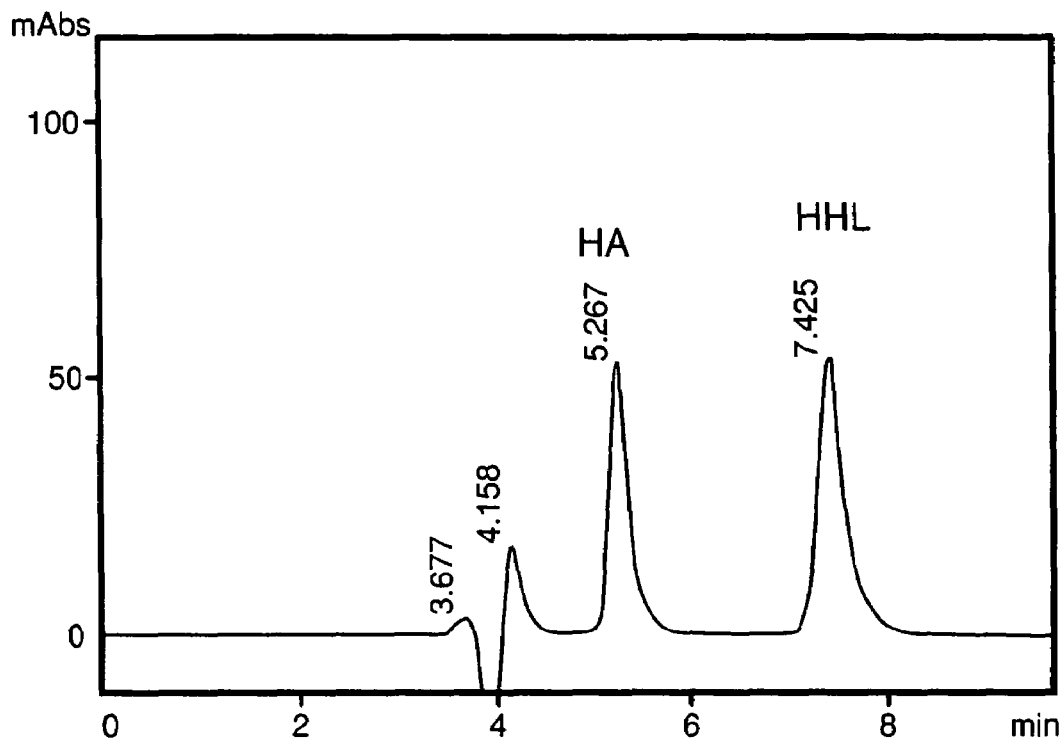
FIG. 1A represents a typical chromatogram for ACE activity.
Figure 1B:
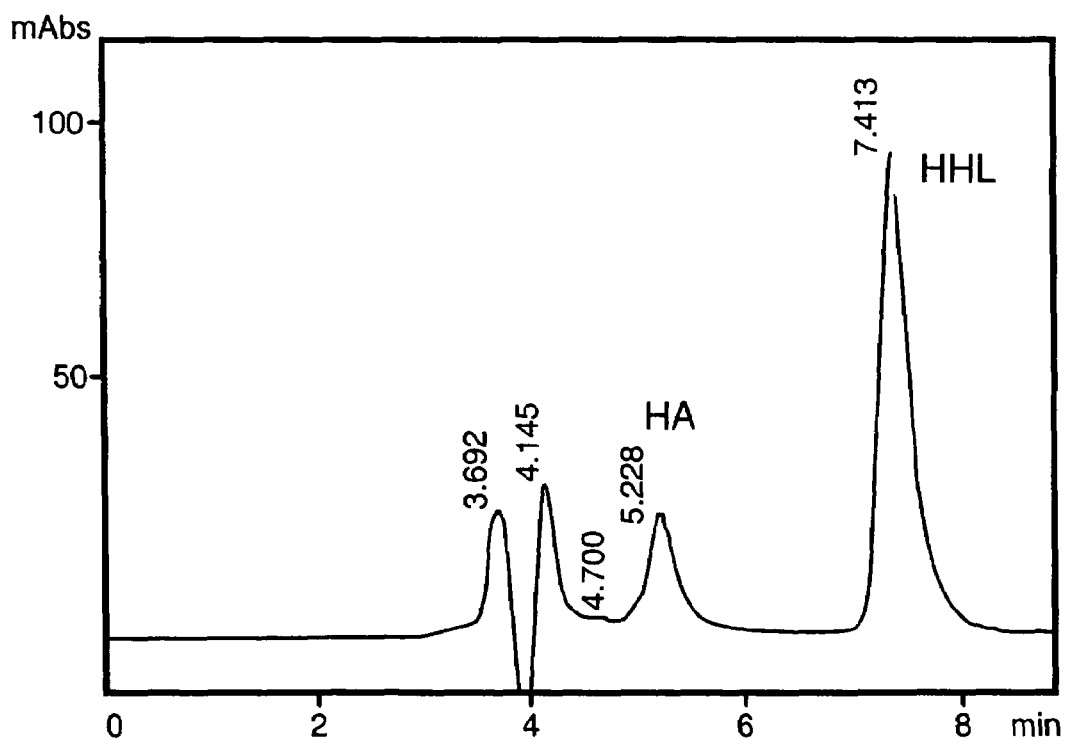
FIG. 1B represents a typical chromatogram for ACE inhibition by hydrolysates/peptide fraction. HA: hippuric acid, HHL: Hippuryl Histidyl Leucine.

In Vitro ACE Inhibitory Activity Determination:

The determination of in vitro ACE inhibitory activity is performed by RP-HPLC modified from the spectrophotometric method described by Cushman and Cheung (1971) ('Spectrophotometric assay and properties of the angiotensin-I converting enzyme of rabbit lung', Biochem. Pharmacol., 20, 1637–1648). ACE was extracted from porcine lung or kidney powder (prepared in the laboratory) with 10-fold (w/v) 100 mM borate buffer (pH 8.3) containing 1% (w/v) NaCl at 4° C. overnight, centrifuged (30 mins, 15,000 rpm, 4° C.). The supernatant was dialyzed against the same buffer for 24 h with two buffer changes. The centrifuge supernatant was used as the source of enzyme. Enzyme activity was assayed by monitoring the released hippuric acid from the substrate, synthetic peptide Hippuryl-His Leu (HHL, Sigma Chemical Co) at 228 nm. The assay mixture contained the following solutions in a total volume of 200 μL: 100 μL 100 mM borate buffer containing 1% NaCl, 50 μL of 5 mM HHL and 25 μL of ACE (units). To determine the inhibition, the hydrolysates or the peptide fractions were pre-incubated with the enzyme. After incubation at 37° C. for 30 mins, the reaction was stopped by adding 250 μL of 1N HCl and centrifuged. The product hippuric acid was separated from HHL by RP-HPLC on a Shimpak Octadecyl column (4.6×250 mm, 5μ) using 50% methanol containing 0.1% TFA at a flow rate of 0.8 mL/min and detected at 228 nm. The typical chromatogram for ACE inhibitory determination of peptides/hydrolysates is shown in FIG. 1. The concentration of the hydrolysates/peptides required to reduce the ACE activity by 50% is defined as the $IC_{50}$ value.

Novel and inventive aspects of the present invention are further explained in the form of following embodiments:

Identifying a plant protein that occurs to an extent of 25–30% in a major oilseed and whose protein sequence is known and which contains the desirable peptide sequences, in a latent state that would be inhibitors of ACE.

Releasing the desired peptides from the protein using proteases whose specificity is varied and well defined.

Obtaining a hydrolysate of glycinin with an $IC_{50}$ of 4.3–5.2 μg $N_2$ for porcine lung and kidney ACE inhibition using fungal protease.

Obtaining a hydrolysate of glycinin with an $IC_{50}$ of 25–30 μg $N_2$ for porcine lung and kidney ACE inhibition using bovine chymotrypsin Obtaining a hydrolysate of glycinin with an $IC_{50}$ of 7–20 μg $N_2$ for porcine lung and kidney ACE inhibition using bovine trypsin Obtaining a hydrolysate of glycinin with an $IC_{50}$ of 30–35 μg $N_2$ for porcine lung and kidney ACE inhibition using plant protease.

Low molecular weight peptides fractions showed greater than 50% inhibition.

A more complete appreciation of the present invention will be realized by reference to the following examples. However, the following examples are not intended to limit the invention disclosed herein but given only by way of illustration.

EXAMPLE 1

5 g of isolated glycinin was dissolved in 50 mL of Tris-HCl buffer, pH 8.2 and incubated at 37° C. for 10 mins. 50 mg of fungal protease (2,260 units/mg protein) was added and incubated for 4 h at 37° C. This was followed by the addition of a second aliquot of 50 mg fungal protease and further incubated 12 h at 37° C. The reaction was stopped by adding 100% TCA to a final concentration of 5% (w/v). The mixture is centrifuged and the supernatant is used for activity tests. The $IC_{50}$ value, a concentration wherein ACE activity is inhibited by 50% of porcine lung ACE was 4.48 μg $N_2$.equivalence

EXAMPLE 2

500 mg of isolated glycinin was dissolved in 2 mL of Tris-HCl buffer, pH 8.2 and incubated at 37° C. for 10 mins. 10 mg of bovine-trypsin (1600 units/mg protein) was added and incubated for 4 h at 37° C. This was followed by the addition of a second aliquot of 10 mg bovine trypsin and further incubated 12 h at 37° C. The reaction was stopped by adding 100% TCA (w/w) to a final concentration of 5%. Centrifuged supernatant is used as peptide source for ACE inhibitory peptides. The $IC_{50}$ value for inhibition of porcine kidney ACE was 18.37 µg $N_2$ equivalence.

EXAMPLE 3

500 mg of isolated glycinin was dissolved in 2 mL of Tris-HCl buffer, pH 8.2 and incubated at 37° C. for 10 mins. 10 mg of bovine chymotrypsin (2,168 units/mg protein) was added and incubated for 4 h at 37° C. This was followed by the addition of a second aliquot of 10 mg bovine chymotrypsin and further incubated 12 h at 37° C. The reaction was stopped by adding 100% TCA (w/w) to a final concentration of 5%. Centrifuged supernatant is used as peptide source for ACE inhibitory peptides. The $IC_{50}$ value for inhibition of porcine lung ACE was 29.0 µg $N_2$ equivalence.

EXAMPLE 4

500 mg of isolated glycinin was dissolved in 2 mL of sodium phosphate buffer, pH 6.0 and incubated at 50° C. for 10 mins. 220 units of ginger protease was added and incubated for 4 h at 50° C. This was followed by the addition of a second aliquot of 100 units of ginger protease and further incubated 12 h at 50° C. The reaction was stopped by adding TCA to a final concentration of 5%. Centrifuged supernatant is used as peptide source for ACE inhibitory peptides. The $IC_{50}$ value for inhibition of porcine kidney ACE was 33.57 µg $N_2$.

EXAMPLE 5

100 mg of isolated glycinin was dissolved in 1 mL of Tris-HCl buffer, pH 8.2 and incubated at 37° C. for 10 mins. 2 mg of bovine chymotrypsin (2,168 units/mg protein) was added and incubated for 8 h at 37° C. This was followed by the addition of a second aliquot of 100 units of ginger protease and further incubated 5 h at 50° C. The reaction was stopped by adding 100% TCA (w/w) to a final concentration of 5%. Centrifuged supernatant is used as peptide source for ACE inhibitory peptides. 50 µL of the supernatant showed 72% inhibition

EXAMPLE 6

Figure 2:
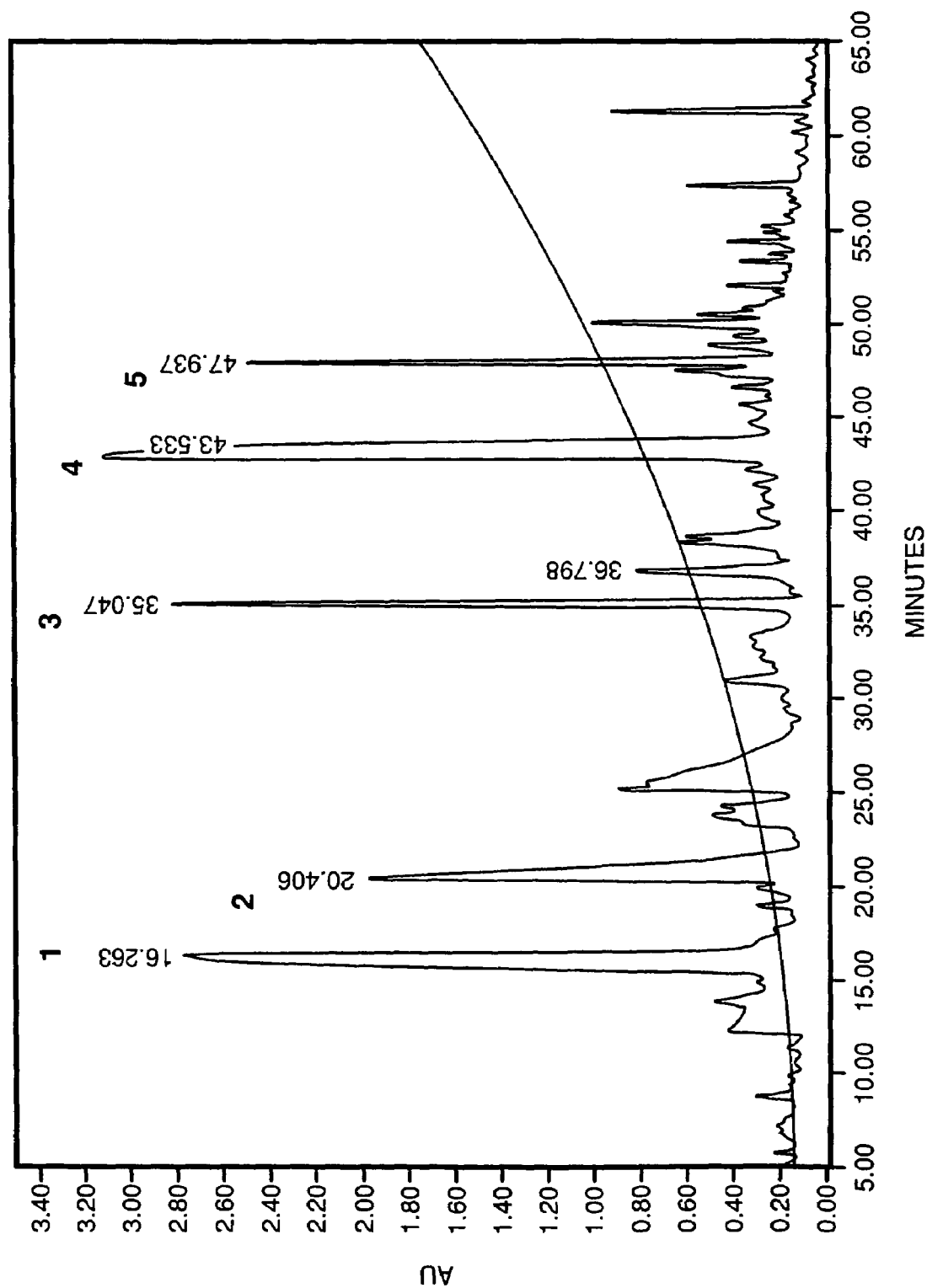
FIG. 2 represents the RP-HPLC profile of the fungal protease digest of glycinin.

500 mg of isolated glycinin was dissolved in 2 mL 0.1M Tris-HCl buffer pH 8.2 and incubated at 37° C. for 5–10 mins. At this stage 2% (w/w) of fungal protease (2,260 units/mg protein) was added and incubated for 18 h. The reaction was stopped by adding 100% TCA (w/v) to a final concentration of 10%, cooled on ice and centrifuged at 15,000 rpm for 30 mins at 4° C. Further the peptides present in the supernatant were separated by RP-HPLC on a C-18 Shimpak column (4.6×250 mm, 5µ) using a gradient of 0.1% TFA and 70% $CH_3CN$ in water containing 0.05% TFA at a flow rate of 0.7 mL/min traversing from 0–35% B. The peptides were detected at 220 nm. Five peptide fractions (as shown in FIG. 2) were collected and used for ACE inhibitory activity. Peptide fraction 2, 3 and 4 showed 66, 81 and 75% inhibition respectively.

Advantages of the Present Invention

1. The raw material for the above process is defatted soy flour with high nitrogen solubility and is available in abundance.
2. The major storage protein of soybean, glycinin, that accounts for 25–35% of the total protein, can be isolated using a minimum number of steps.
3. The amino acid sequence of glycinin is known. Glycinin is a source of ACE inhibitory peptides, which are latent in the known sequence.
4. These peptides can be released from glycinin by a variety of proteases with varying and well-defined specificities. These peptides are potent inhibitors of porcine lung and kidney ACE in vitro.

The invention claimed is:

1. A process for the preparation of Angiotensin Converting Enzyme (ACE) inhibitory peptides from glycinin, said process comprising the steps of:
    (a) isolating glycinin from defatted soy flour;
    (b) dispersing a 10–25% solution of glycinin in a buffer;
    (c) hydrolyzing the mixture of glycinin and buffer with 2–4% w/v of one or more proteolytic enzymes;
    (d) incubating the mixture at 37–50° C. for a period of 16–18 hours;
    (e) arresting the hydrolysis reaction by adding trichloroacetic acid to the mixture;
    (f) centrifuging the mixture at 15–20,000 rpm for 30–40 minutes, at a temperature of about 4–8° C.;
    (g) obtaining from the centrifugation supernatant a mixture of protein hydrolysates containing polypeptides; and
    (h) separating and purifying from the mixture of protein hydrolysates peptide fractions having ACE inhibitory activity of 66%, 81% and 75%.
2. The process of claim 1, wherein the buffer of step (b) is selected from Tris-HCl and sodium phosphate.
3. The process of claim 1, wherein the mixture in step (c) is hydrolyzed with a mixture of proteolytic enzymes.
4. The process of claim 1, wherein the proteolytic enzyme comprises a plant protease having the specificity of cleaving C-terminal to proline.
5. The process of claim 1, wherein the proteolytic enzyme is selected from the group consisting of bovine trypsin, bovine chymotrypsin, plant protease, and a protease from ginger (*Zingiber officinale*), or a combination thereof.
6. The process of claim 1, wherein the step (h) is performed by RP-HPLC on an octadecyl column using a linear gradient of 0.05–0.1% trifluoroacetic acid and 0–70% acetonitrile.
7. The process of claim 1, wherein the peptide fractions having ACE inhibitory activity have an $IC_{50}$ value for in vitro ACE inhibition in the range of 5–39 µg $N_2$ equivalence.

* * * * *